(12) United States Patent
Braslau

(10) Patent No.: US 8,975,014 B2
(45) Date of Patent: *Mar. 10, 2015

(54) FLUORESCENCE DETECTION OF POISON OAK OIL

(71) Applicant: The Regents of the University of California, Oakland, CA (US)

(72) Inventor: Rebecca Braslau, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/270,985

(22) Filed: May 6, 2014

(65) Prior Publication Data

US 2014/0242712 A1    Aug. 28, 2014

Related U.S. Application Data

(63) Continuation of application No. 13/714,899, filed on Dec. 14, 2012, now Pat. No. 8,735,057, which is a continuation of application No. 12/736,814, filed as application No. PCT/US2009/002958 on May 13, 2009, now Pat. No. 8,389,232.

(60) Provisional application No. 60/127,588, filed on Apr. 2, 1999.

(51) Int. Cl.
| | |
|---|---|
| *C12Q 1/00* | (2006.01) |
| *G01N 33/00* | (2006.01) |
| *G01N 33/50* | (2006.01) |
| *A61K 31/69* | (2006.01) |
| *A61K 49/00* | (2006.01) |
| *G01N 33/52* | (2006.01) |

(52) U.S. Cl.
CPC ............... *G01N 33/50* (2013.01); *A61K 31/69* (2013.01); *A61K 49/0006* (2013.01); *A61K 49/0019* (2013.01); *G01N 33/52* (2013.01); *A61K 49/0021* (2013.01); *Y10S 435/81* (2013.01)
USPC ............ 435/4; 436/93; 436/96; 436/106; 436/111; 436/116; 435/810

(58) Field of Classification Search
CPC .............. A61K 31/69; A61K 49/0006; A61K 49/0019; A61K 49/0021; G01N 33/52
See application file for complete search history.

(56) References Cited

U.S. PATENT DOCUMENTS

| | | | |
|---|---|---|---|
| 7,069,926 B2 * | 7/2006 | Skellern et al. | 128/200.14 |
| 7,112,572 B2 * | 9/2006 | Deadman et al. | 514/13.7 |
| 8,735,057 B2 * | 5/2014 | Braslau | 435/4 |

FOREIGN PATENT DOCUMENTS

WO   WO 2007124543   * 11/2007

* cited by examiner

*Primary Examiner* — Chris R Tate
*Assistant Examiner* — Douglas F White
(74) *Attorney, Agent, or Firm* — Matthew Kaser; Adam Warwick Bell

(57) ABSTRACT

The invention herein disclosed provides for compositions, methods for synthesizing said compositions, and methods for using said compositions, wherein the compositions and methods may be used to bind to and/or deactivate a poison oak oil, such as urushiol. The compositions and methods can be used to treat and/or reduce an inflammatory reaction and/or hypersensitivity to natural compounds found in poison oak, poison ivy, poison sumac, mango, lac tree, and cashew nut.

23 Claims, 14 Drawing Sheets

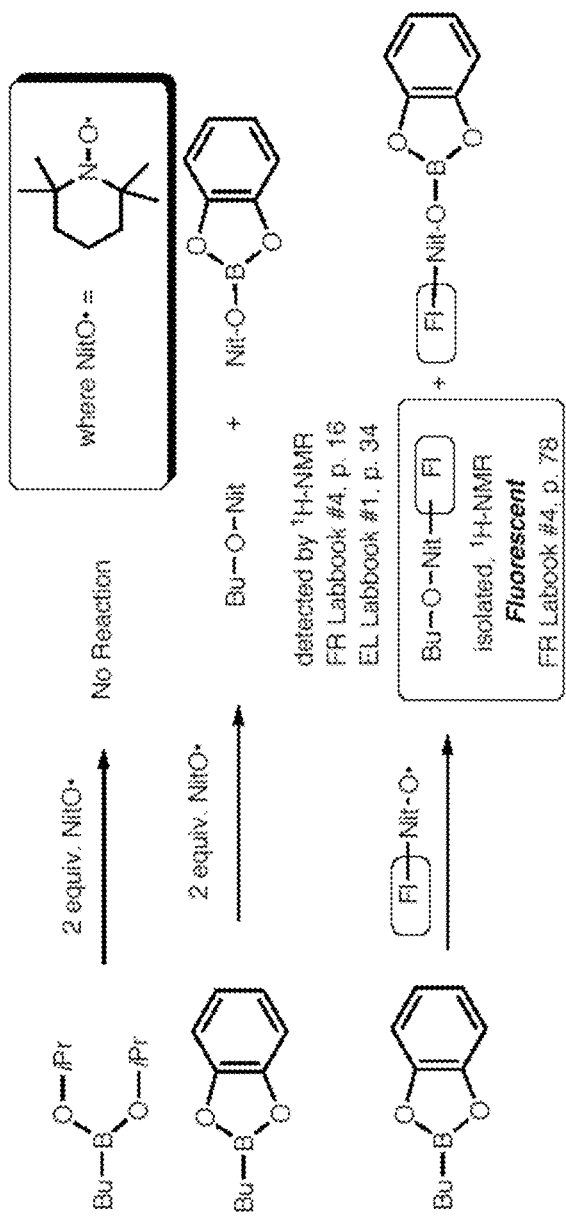
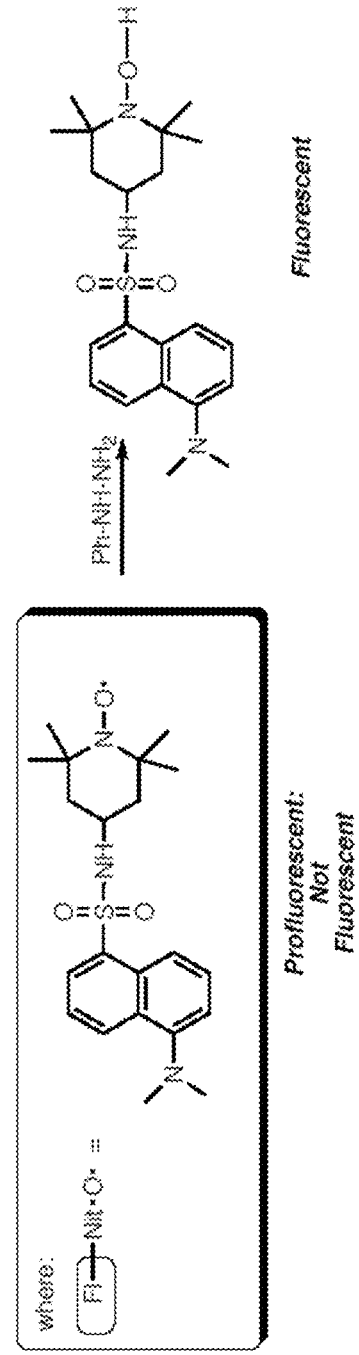
FIGURE 7A
FIGURE 7B

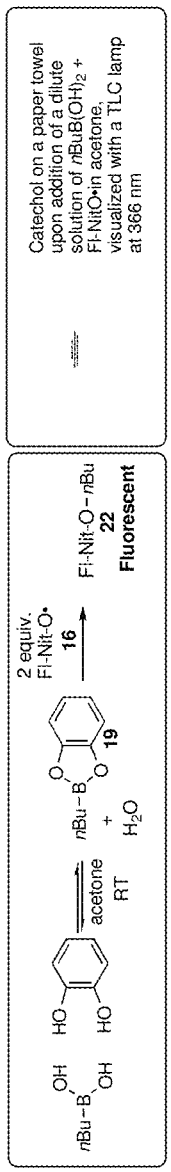
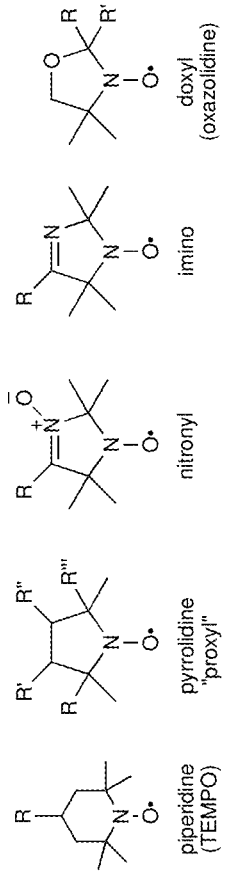
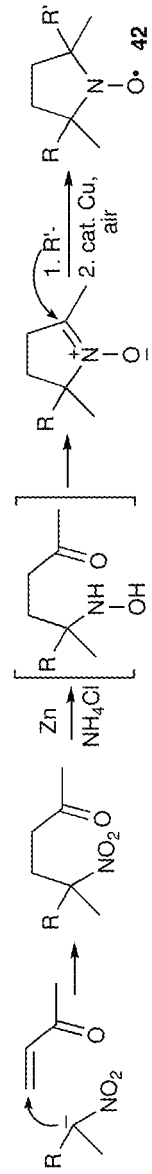
A B
FIGURE 15
FIGURE 16
FIGURE 17

FLUORESCENCE DETECTION OF POISON OAK OIL

This application is a Continuation patent application of copending U.S. application Ser. No. 13/714,899, filed 14 Dec. 2012, which was a Continuation U.S. patent application Ser. No. 12/736,814, filed 12 Nov. 2010.

RELATIONSHIP TO OTHER APPLICATIONS

This application claims priority to and benefits of the following: U.S. Provisional Patent Application No. 60/127,588, filed 13 May 2008, entitled "Fluorescence Detection And Deactivation Of Poison Oak Oil", International Patent Application number PCT/US2009/002958, filed 13 May 2009, entitled "Fluorescence Detection And Deactivation Of Poison Oak Oil", U.S. National Phase patent application Ser. No. 12/736,814, filed 12 Nov. 2010, entitled "Fluorescence Detection And Deactivation Of Poison Oak Oil", and U.S. Continuation patent application Ser. No. 13/714,899 filed 14 Dec. 2012, entitled "Fluorescence Detection And Deactivation Of Poison Oak Oil", each of which is herein incorporated by reference in its entirety for all purposes.

This invention was made partly using funds from United States National Science Foundation (NSF) research grant No. CHE-0453126. The Federal Government has certain rights to this invention.

FIELD OF THE INVENTION

The invention provides compositions, kits, and methods of using the compositions and kits for detecting, deactivating, degrading, immunogenic compounds from poison oak and poison ivy.

BACKGROUND

Urushiol-induced allergic contact dermatitis in the United States most commonly results from unexpected exposure to oils from plants in the sumac Family Anacardiaceae. Approximately 10 to 50 million Americans suffer from rashes resulting from exposure every year. In particular, the genus *Toxicodendron* species (which include Western and Eastern poison oak *T. diversilobum*, poison ivy *T. radicans*, and poison sumac or dogwood *T. vernix*) are distributed widely across North America. Other sources of urushiol include poison wood (in Florida and the Bahamas), and the sap (kiurushi) of the Asian lacquer tree (*Toxicodendron verniciflua*) used as a varnish in Japanese lacquer ware, and cashew nut shells. (See, for example, Tucker and Swan (1998) NEJM, 339(4): 235.)

Reaction to urushiol is an immunological response to the bio-oxidized form of urushiol (the ortho-quinone). Approximately 50-70% of the U.S. population is either allergic to urushiol, or will become allergic to it upon sensitization by repeated exposure. Symptoms of allergic contact dermatitis from urushiol exposure (often referred to as Rhus dermatitis) vary from a mild annoyance to weeks of irritation and pain. Occasionally, exposure can lead to nephropathy and even to fatal systemic anaphylaxis. The monetary cost due to worker disability from urushiol-induced injuries is substantive: in the states of California, Washington and Oregon, it has been estimated that up to one third of forestry workers are temporarily disabled by poison oak dermatitis each year. In California, the medical costs associated with poison oak injuries accounts for up to 1% of the annual workers' compensation budget. It has been estimated that *Toxicodendron* dermatitis is responsible for 10% of the total U.S. Forest Services lost-time injuries. In 1988, NIOSH estimated that 1.07-1.65 million occupational skin injuries occurred yearly, with an estimated annual rate of 1.4 to 2.2 cases per 100 workers (8) the costs attributable to lost productivity, medical payments, and disability payments are very high. (See U.S. Centers for Disease Control; Leading work-related diseases and injuries—United States. MMWR, 1986 335:561-563).

Chemically, urushiol is a name given to a collection of related compounds that are 3-substutitued catechols (1,2-benenediols), in which the long hydrophobic chain is a linear $C_{15}$ or $C_{17}$ alkyl chain containing 0-4 degrees of cis unsaturation (FIG. 1). The catechols with two, three, and four carbon-carbon double bonds (2-4 degrees of unsaturation) seem to be the most virulent in eliciting an allergic response. Each of the different members of the *Toxicodendron* species contain mixtures of the $C_{15}$ or $C_{17}$ alkyl chains, with various degrees of unsaturation.

They all share the catechol functionality in common, and a long, greasy alkyl chain that facilitates migration into the skin. In addition to direct contact with the toxic plants, exposure commonly occurs by transfer from animal fur, contaminated clothing, garden tools, fire-fighting equipment, forestry and sports equipment. There are a few commercially available products that can be applied prophylactically to protect the skin by creating a physical barrier using organoclays (for example, a lotion containing quaternium-18 bentonite is commercially available as IVYBLOCK from Enviroderm Pharmaceuticals, Inc.). However, the success of this strategy requires advanced planning. By far the majority of allergic contact dermatitis cases from urushiol result from unexpected exposure.

A number of methods to treat poison ivy or poison oak have been investigated, including hyposensitization, but this process is involved and can have unfavorable side effects. Studies towards an immunological approach to desensitization have been pursued, but have not yet reached a level of practical application. The best treatment to date is to avoid contact with urushiol. As most patients are unaware that they have had contact with urushiol, a low cost, quick and inexpensive method of detection is warranted. There are many recommended methods to remove urushiol after recent contact, including water, soapy water, organic solvents, and a variety of commercially available solubilizing mixtures including TECHNU, IVYCLEANSE, ALL-STOP, ZANFEL (comprising fatty acid, alcohol, and the surfactant sodium lauroyl sarcosinate), and even DIAL ultra dishwashing soap. Thus the ability to detect urushiol before it transverses the skin will be extremely valuable in mitigating the suffering caused by contact with the various *Toxicodendron* species. In addition, continued re-exposure (chronic exposure) from repeated introduction of the oil to the patient (from door handles, shoelaces, etc.) is a considerable problem. As little as 0.001 mg of urushiol is enough to cause allergic contact dermatitis.

Treatment of the contact dermatitis usually involves a course of topical and/or enteric treatments with hydrocortisones, β-methasone, and other similar corticosteroids. Repeated exposure to either the original allergen or to a similar allergen can result in a severe hypersensitive immunoreaction, that is often extremely painful and, occasionally, fatal. There is therefore a particular need in the art for compounds and methods of treatment that can remove the allergen(s) prior to induction of an immune and/or allergic response, that can prevent the binding of the allergen(s) to an immunoglobulin or a cell-surface receptor, and/or that can be used to rapidly detect the presence of such allergen(s) so that other precautions may be used to remove the allergen(s) from the area of contact.

There is therefore a need in the art to provide for compositions and methods for detecting the presence of urushiol, inactivating urushiol, and removing urushiol from substrates (including, for example, skin and clothing).

BRIEF DESCRIPTION OF THE INVENTION

The invention is drawn to novel methods, kits, sprays (including aerosol sprays) and compositions for detecting active compounds present in oils that are found in poison oak, poison ivy, poison sumac, cashew nut, and related plants. The methods disclosed herein may also be used to detect other catechols, both synthetic and those found in nature. The invention also is drawn to compositions that may be used to detect said active compounds using fluorescence. In one embodiment the methods of the invention may be used to detect catechols and alkyl-substituted catechols, such as, for example, urushiol, catechin, epicatechin, gallocatechin, epigallocatechin, epigallocatechin-3-gallate, and the like; and chatecholamines, such as, for example, epinephrine, norepinephrine, dopamine, dihydroxyphenylalanine (DOPA), and the like.

The invention provides methods for detecting, treating, and deactivating the antigenic and/or allergenic compounds that induce urushiol-induced contact dermatitis. In one embodiment the method may be used for treating, deactivating, and/or detecting alk(en)yl catechols, and/or alk(en)yl resorcinols.

The invention may be used by clinicians, nursing staff, paramedics, emergency rescue team members, the military, firefighters, forestry personnel, lumberworkers, hunters, mountaineers, hikers, anglers, and the like. In one embodiment, the invention is a kit comprising the elements disclosed herein and a set of instructions of how to use the kit, wherein the kit is used for detecting, treating, and/or deactivating a catechol. The kit can be used, for example, in the home, in the field, in a camp, in a clinic, in a hospital, in an emergency room, and the like.

The invention provides a kit for detecting a catechol, the kit comprising a vessel, the vessel shaped and adapted for confining a composition, the composition further comprising a boron composition, a first nitroxide, and a second nitoxide, and an applicator. In one embodiment the boron composition comprises a hydrophobic alkyl group. In another embodiment the second nitroxide is a profluorescent nitroxide. In a preferred embodiment the applicator is a spray applicator. In a most preferred embodiment the catechol is urushiol. In one alternative embodiment, the kit can also comprise an aerosol propellant. In another embodiment the kit comprises a lamp.

In a preferred embodiment, the invention provides a method for detecting a catechol in a sample, the method comprising the steps of (i) contacting a boron composition and a nitroxide with the sample (ii) allowing the boron composition to react with the catechol in the sample thereby creating a catecholborane; (iii) allowing a first nitroxide to react with the catecholborane thereby generating an alkyl radical and a nitroxide-catecholborane complex; (iv) allowing the alkyl radical to react with a second nitroxide thereby creating an alkoxyamine; (v) measuring the amount of alkoxyamine, nitroxide-catecholborane complex, or an alkoxyamine hydrolysis product so created; the method resulting in detecting the catechol in the sample. In one embodiment the boron composition comprises a hydrophobic alkyl group. In a preferred embodiment, the catecholborane is a B-alkyl catecholborane. In another preferred embodiment the alkyl group is selected from the group consisting of a hydrophobic alkyl group and a hydrophilic alkyl group. In a yet alternative embodiment the nitroxide is a profluorescent nitroxide. More preferably, the nitroxide is tetramethylpiperidinyloxy (TEMPO). In a more preferred embodiment the profluorescent nitroxide is dansyl amino-TEMPO. In another preferred embodiment the sample is selected from the group consisting of an area of a subject's skin, clothing, boots, pets, camping gear, tools, and other outdoor equipment. In another preferred embodiment the sample is selected from the group consisting of a plant tissue, a plant extract, a plant tissue extract, an animal tissue, an animal extract, an animal tissue extract, and an animal fluid. In a more preferred embodiment the plant tissue is from a plant selected from the group consisting of poison oak, poison ivy, poison sumac, mango, cashew nut, and lac tree.

The invention further provides the methods as disclosed herein wherein the nitroxide further comprises a fluorescent compound, the fluorescent compound selected from the group consisting of a hydrophobic fluorescent organic molecule, a hydrophilic fluorescent organic molecule, and a fluorescent quantum-dot nanoparticle.

In one embodiment the method comprises the measuring the amount of alkoxyamine so created using a photon source that results in fluorescence of the alkoxyamine and the nitroxide-catecholborane complex, wherein the fluorescence is visible to the naked eye. In a preferred embodiment the measuring of the amount of alkoxyamine so created is performed using a photon source that induces fluorescence of the alkoxyamine and the nitroxide-catecholborane complex, wherein the fluorescence is detected by a photometer. In a more preferred embodiment the fluorescence comprises photons having a wavelength of between about 250 and 600 nm. In one embodiment the photon source is a lamp. In a preferred embodiment the lamp is a hand-held lamp. In an alternative embodiment the photon source is the sun. The method may also further comprise measuring hydroxylamine complexed with boron or free hydroxylamine created by hydrolysis.

In a preferred embodiment of the invention the catechol is selected from the group consisting of urushiol, catechin, epicatechin, gallocatechin, epigallocatechin, epigallocatechin-3-gallate, and catecholamines epinephrine, norepinephrine, dopamine, and dihydroxyphenylalanine (DOPA). In a more preferred embodiment the catechol is urushiol.

The method may further comprise the step of reacting the alkyl radical with a profluorescent nitroxide having a fluorescent tag, wherein the fluorescent tag is selected from the group consisting of an organic fluorophore and Cd—Se nanoparticle. In another embodiment the method may further comprise the step of measuring the amount of the nitroxide-catecholborane complex. In another embodiment the method further comprises the step of measuring the amount of hydroxylamine hydrolysis product. In a yet other embodiment the method further comprises the step of measuring the amount of alkoxyamine product.

The invention also provides for a method for deactivating a catechol in a sample, the method comprising the steps of (i) contacting a boron composition and an oxygen-containing molecule with the sample (ii) allowing the boron composition to react with the catechol in the sample thereby creating a catecholborane; the method resulting in deactivating the catechol in the sample. In one embodiment the boron composition comprises a hydrophobic alkyl group. In a preferred embodiment, the catecholborane is a B-alkyl catecholborane. In another preferred embodiment the alkyl group is selected from the group consisting of a hydrophobic alkyl group and a hydrophilic alkyl group. In a yet alternative embodiment the nitroxide is a profluorescent nitroxide. More preferably, the nitroxide is tetramethylpiperidinyloxy (TEMPO). In a more preferred embodiment the profluorescent nitroxide is dansyl amino-TEMPO. In another preferred embodiment the sample is selected from the group consisting of an area of a subject's skin, clothing, boots, pets, camping gear, tools, and other outdoor equipment. In another preferred embodiment the sample is selected from the group consisting of a plant tissue, a plant extract, a plant tissue extract, an animal tissue, an animal extract, an animal tissue extract, and an animal fluid. In a more preferred embodiment the plant tissue is from a plant selected from the group consisting of poison oak, poison ivy, poison sumac, mango, cashew nut, and lac tree.

In one preferred embodiment the oxygen-containing molecule comprises a nitroxide. The invention further provides the methods as disclosed herein wherein the nitroxide further optionally comprises a fluorescent compound, the fluorescent compound selected from the group consisting of a hydrophobic fluorescent organic molecule, a hydrophilic fluorescent organic molecule, and a fluorescent quantum-dot nanoparticle.

In one embodiment the method comprises the measuring the amount of alkoxyamine so created using a photon source that results in fluorescence of the alkoxyamine and the nitroxide-catecholborane complex, wherein the fluorescence is visible to the naked eye. In a preferred embodiment the measuring of the amount of alkoxyamine so created is performed using a photon source that induces fluorescence of the alkoxyamine and the nitroxide-catecholborane complex, wherein the fluorescence is detected by a photometer. In a more preferred embodiment the fluorescence comprises photons having a wavelength of between about 250 and 600 nm.

The method may also further comprise measuring hydroxylamine complexed with boron or free hydroxylamine created by hydrolysis.

In a preferred embodiment of the invention the catechol is selected from the group consisting of urushiol, catechin, epicatechin, gallocatechin, epigallocatechin, epigallocatechin-3-gallate, and catecholamines epinephrine, norepinephrine, dopamine, and dihydroxyphenylalanine (DOPA). In a more preferred embodiment the catechol is urushiol.

The invention also provides for a boron composition, the boron composition comprising a reactive moiety that reacts with a catechol with a rate constant, k, of at least $0.2\ M^{-1}s^{-1}$ and wherein the reaction produces a stable chatecholborane.

The invention provides for a pharmaceutical composition, the pharmaceutical composition comprising a boron composition, wherein the boron composition comprises a hydrophobic alkyl group. In one embodiment the alkyl group is selected from the group consisting of a hydrophobic alkyl group and a hydrophilic alkyl group. In another embodiment the pharmaceutical composition comprises a boron composition in an effective amount for the treatment of poison oak oil-induced contact dermatitis. In a preferred embodiment the poison oak oil comprises a catechol. In a more preferred embodiment the catechol is urushiol.

The invention provide a topical composition, the topical composition comprising an effective amount of a boron composition and a suitable excipient, carrier, or combination thereof, the boron composition comprising an alkylboronic acid having the general formula $R-B(OH)_2$. In one alternative embodiment the boron composition optionally comprises at least one B-alkyl boronic acid derivative. In another embodiment the topical composition optionally containing xanthan gum or gellan gum. In a more preferred embodiment the boron composition is present in an amount selected from the group consisting of from about 99.5% to about 0.001%, from about 95% to about 0.1%, and from about 90% to about 0.5%, by weight, based on the total combined weight of the boron composition thereof, not including other excipient, carrier, or combination thereof. In a most preferred embodiment the topical composition comprises a boron composition in an effective amount for the detection of a catechol in poison oak oil.

The invention further provides a topical medicament, the topical medicament comprising a boron composition, the boron composition comprising an alkylboronic acid having the general formula $R-B(OH)_2$, a nitroxide, and a suitable excipient, carrier, or combination thereof, and where R is selected from the group consisting of a hydrophobic alkyl group and a hydrophilic alkyl group. In an alternative embodiment the boron composition optionally comprises at least one B-alkyl boronic acid derivative. In a more preferred embodiment the nitroxide is a profluorescent nitroxide. In a more preferred embodiment the topical medicament comprises a boron composition in an effective amount for the detection of a catechol in poison oak oil to avoid induced contact dermatitis. In another more preferred embodiment the topical medicament comprises a boron composition in an effective amount for the treatment of poison oak oil-induced contact dermatitis.

In one embodiment, the invention provides a method for detecting, treating, and deactivating alk(en)yl catechols, and/or alk(en)yl resorcinols using a boron compound bearing a hydrophobic alkyl group and an at least one equivalent of profluorescent nitroxide are that are mixed in solution or on a substrate. In one preferred embodiment, the profluorescent nitroxide is a nitroxide with a short tether to a fluorescent dye, wherein the dye is quenched in the presence of the free nitroxide. In an alternative embodiment the boron compound further comprises an alkyl boronic acid or alkyl boronic acid derivative. In another alternative embodiment the boron compound further comprises at least one leaving group. In yet another alternative embodiment, the boron compound further comprises two leaving groups.

In one embodiment the invention provides a method for detecting, treating, and deactivating alk(en)yl catechols, and/or alk(en)yl resorcinols, wherein the method results in producing a fluorescent compound that fluoresces when illuminated and wherein the fluorescence is induced by photons having a wavelength of between about 250 and 600 nm. In one embodiment the fluorescence can be, for example, between 250 and 300 nm, between 300 and 350 nm, between 350 and 400 nm, between 450 and 500 nm, between 500 and 550 nm, and between 550 and 600 nm. In the alternative, the method results in producing a fluorescent compound that fluoresces when illuminated with light in the visible spectrum and wherein the fluorescence is induced by photons having a wavelength of between about 600 and 750 nm. In one embodiment the fluorescence can be, for example, between 600 and 650 nm, between 650 and 700 nm, and between 700 and 750 nm.

In another alternative embodiment, the nitroxide can comprise a fluorescent tag such as, for example, a fluorescent organic compound, such as dansyl, 3-hydroxy-2-methyl-4-quinolinecarboxylic ester, a coumarin, a xanthene, a cyanine, a pyrene, a borapolyazaindacene, an oxazine, bimane, 4-acetamido-4'-isothiocyanatostilbene-2,2'-disulfonic acid (SITS) and related stilbene derivatives, and the isothiocyanate of pyrenetrisulfonic acid, fluorescein, acryoldan, rhodamine, dipyrromethaneboron difluoride (BODIPY), acridine orange, eosin, acridine orange, 1-(3-(succinimidyloxycarbonyl)benzyl)-4-(5-(4-methoxyphenyl)oxazol-2-yl)pyridinium bromide (PyMPO), alexa fluor 488, alexa fluor 532, alexa fluor 546, alexa fluor 568, alexa fluor 594, alexa fluor 555, alexa fluor 633, alexa fluor 647, alexa fluor 660 and alexa fluor 680, or the like, or a quantum-dot nanoparticle. In the present invention, a non-limited list of quantum dot nanoparticles includes cadmium sulfide (CdS), cadmium selenide (CdSe), zinc sulfide (ZnS), zinc oxide (ZnO), lead sulfide (PbS), zinc selenide (ZnSe), GaAS, and InP. (Lakowicz et al., Anal. Biochem., 2000, 280: 128-136.

The invention further provides use of a composition comprising a boron composition for the manufacture of a composition for detecting a catechol. In one embodiment the boron composition comprises an alkylboronic acid having the general formula $R-B(OH)_2$, a nitroxide, and a suitable excipient, carrier, or combination thereof, and where R is selected from the group consisting of a hydrophobic alkyl group and a hydrophilic alkyl group. In one alternative embodiment the boron composition optionally comprises at least one B-alkyl boronic acid derivative. In a preferred embodiment the nitroxide is a profluorescent nitroxide. In another preferred embodiment the composition comprises a boron composition in an effective amount for the detection of a catechol in poison oak oil.

The invention can be used in a variety of embodiments, for example, for use as chemical sensors and molecular specific deactivating agents. The invention can be used in phototherapy for treatment of an inflammatory response and other disorders. The invention can also be used as a sensor that detects molecules. The invention is of particular use in the fields of clinical diagnosis, clinical therapy, clinical treatment, and clinical evaluation of various diseases and disorders, in the field of consumer goods, for example, over-the-counter medications, balms, ointments, etc., and diagnostic kits, manufacture of compositions for use in the treatment of various diseases and disorders, for use in molecular biology, structural biology, cell biology, molecular switches, molecular circuits, and molecular computational devices, and the manufacture thereof.

In one embodiment, the composition comprises a surface stabilizer. In another alternative embodiment the composition comprises at least two surface stabilizers. In a preferred embodiment, the surface stabilizer is selected from the group consisting of an anionic surface stabilizer, a cationic surface stabilizer, a zwitterionic surface stabilizer, and an ionic surface stabilizer.

In another preferred embodiment, the surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptylβ-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-phospholipid, PEG-cholesterol, PEG-cholesterol derivative, and PEG-vitamin A.

In another alternative embodiment, the cationic surface stabilizer is selected from the group consisting of a polymer, a biopolymer, a polysaccharide, a cellulosic, an alginate, a nonpolymeric compound, and a phospholipid.

In another alternative embodiment, the surface stabilizer is selected from the group consisting of cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$ dimethyl hydroxyethyl ammonium chloride, $C_{12-15}$-dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)4 ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethylbenzyl ammonium chloride, N-tetradecylidmethylbenzy-1 ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammoniumchloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts; amines, amine salts, amine oxides, imide azolinium salts, protonated quaternary acrylamides, methylated quaternary polymers, and cationic guar.

The invention also provides for a chemical spray that can be used in the field to allow the detection of urushiol in conjunction with the use of a fluorescent lamp. In one embodiment the amount of urushiol detected is in the range of between about 0.1-100 µg. In a preferred embodiment, the amount of urushiol detected is in the range of between about 1-10 µg.

BRIEF DESCRIPTION OF THE DRAWINGS

FIG. 7A illustrates details of another exemplary reaction between either a borane compound (top), a catecholborane (middle and bottom), and a nitroxide or profluorescent nitroxide that results in no reaction (top), production of a nitroxide-catecholborane (middle), or production of a fluorescent nitroxide-catecholborane (bottom). FIG. 7B illustrates details of how a reaction between a profluorescent nitroxide in the presence of phenylhydrazine results in production of a fluorescent compound.

FIG. 15 shows the in situ formation of n-butylcatecholborane 19 and subsequent reaction to form fluorescent 22 (A) in one pot (B).

FIG. 16 illustrates common classes of readily synthesized stable nitroxides.

FIG. 17 illustrates a general synthesis pioneered by Hideg and Keana for the preparation of proxyl nitroxides 42.

DETAILED DESCRIPTION OF THE INVENTION

Figure 1:
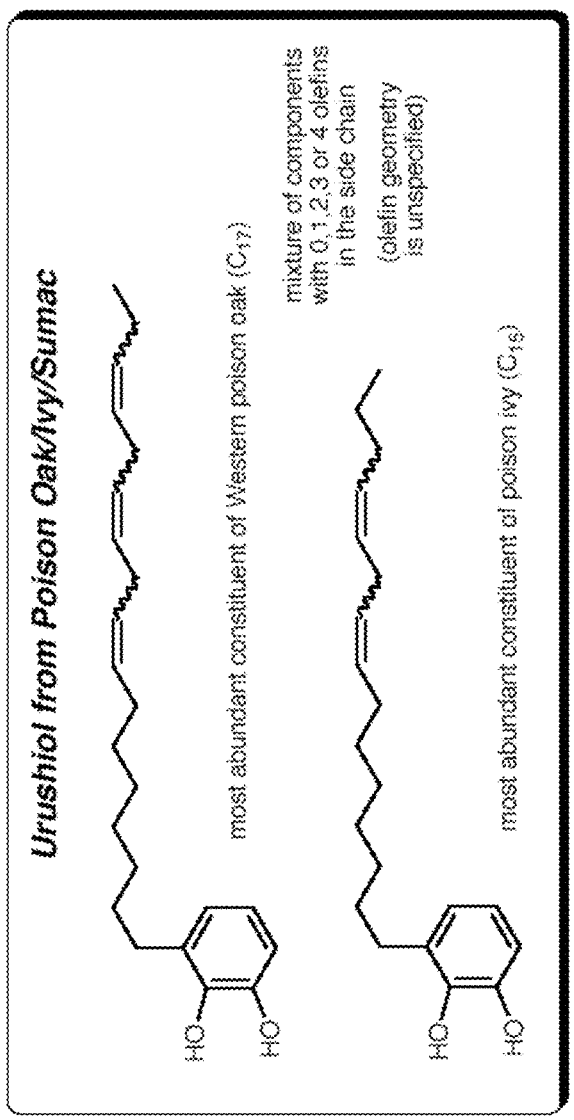
FIG. 1 illustrates the chemical formulae of chatechol and exemplary urushiols.
Figure 2:
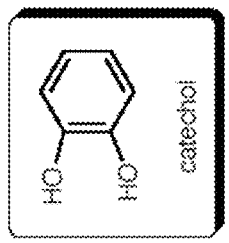
FIG. 2 illustrates how B-alkyl catechol borane species react with oxygen radicals to expel alkyl radicals (adapted from Darency and Renaud, 2006, Top. Curr. Chem., 263: 71-106; Cadot et al. 2002, JOC, 67: 7193-7202; Baban et al. 1986, J. Chem. Soc., Perkin Trans. 2: 157).
Figure 2:
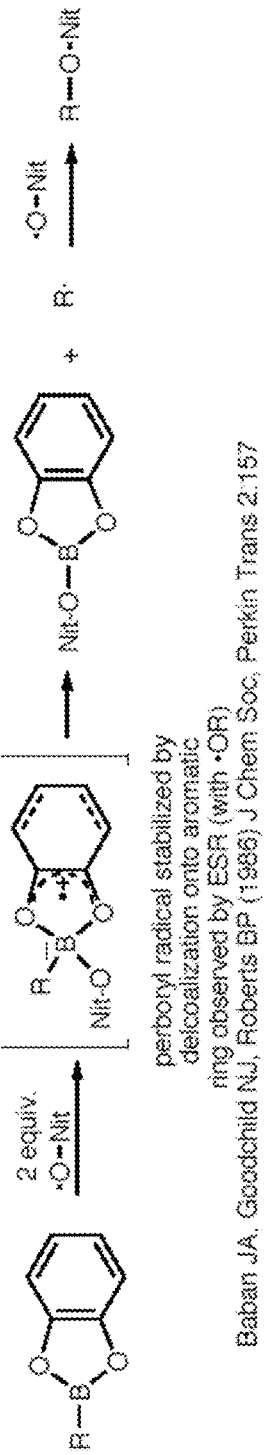
Figure 3:
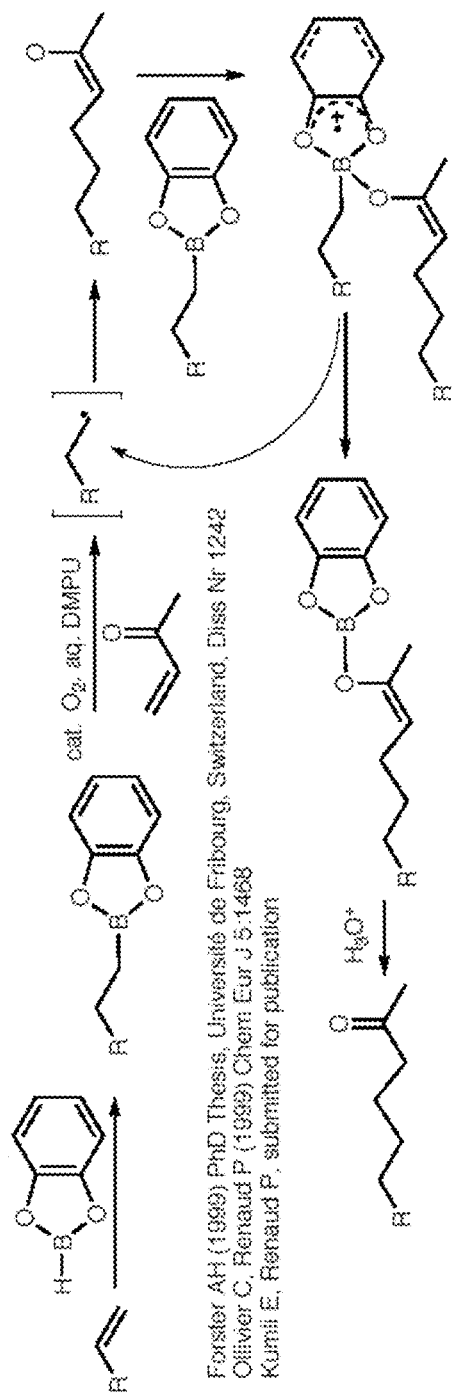
FIG. 3 illustrates a modified Brown and Negishi reaction that may comprise chain transfers with PTOC-OMe for radical acceptors (Brown and Negishi, 1971, J. Am. Chem. Soc. 93: 3777; Suzuki et al. 1969, J. Chem. Soc., Chem. Commun., 17: 1009; Forster 1999, PhD Thesis, University de Fribourg, Switzerland, Diss Nr. 1242; Ollivier and Renaud 1999, Chem. Eur. J., 5: 1468; Kumli and Renaud, 2006, Org. Lett. 8: 5861; Olivier and Renaud, 2000, Angew. Chem. Int. Ed. 39: 925).
Figure 4:
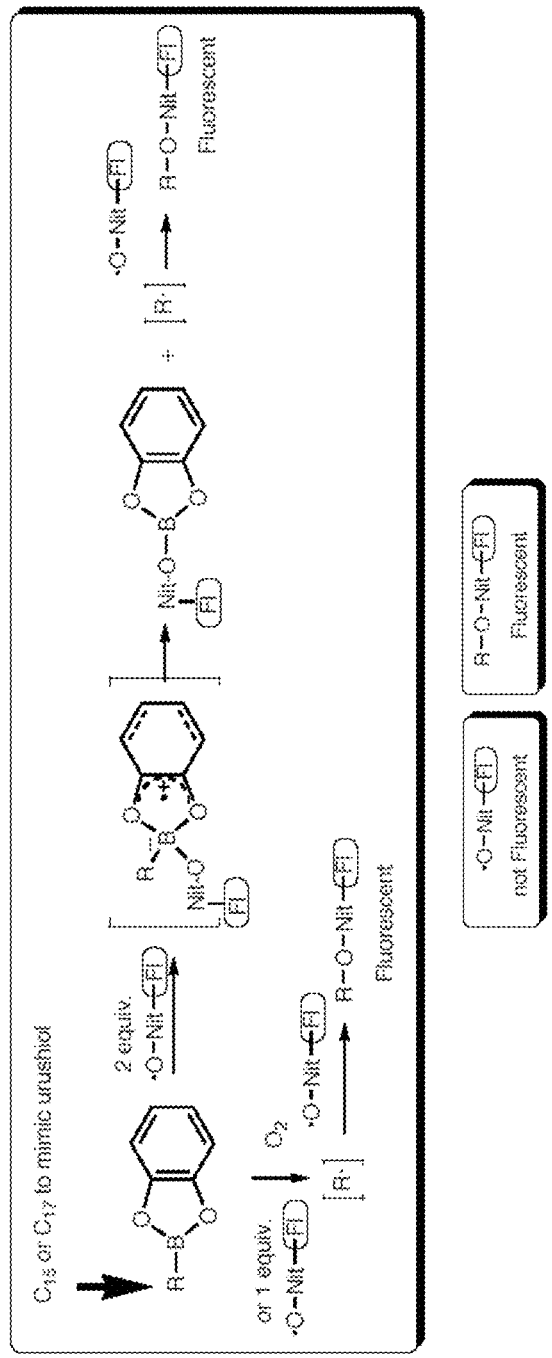
FIG. 4 illustrates novel methods for detecting poison oak oil (including poison ivy, sumac oil, and lac tree extracts) that are present upon a substrate by chemical generation of fluorescence.
Figure 5:
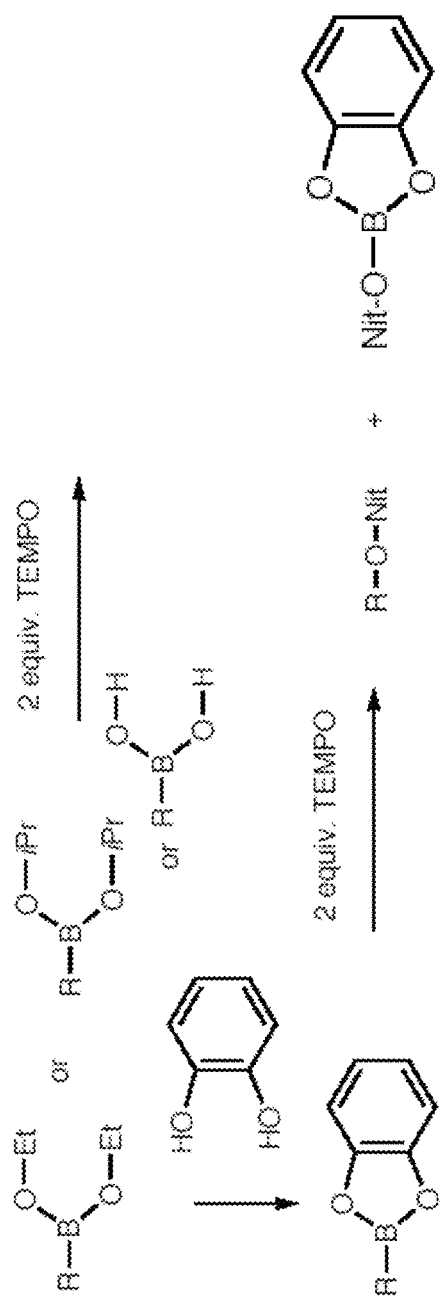
FIG. 5 illustrates an exemplary reaction between a nitroxide (for example, TEMPO) and a catechol that results in a nitroxide-catecholborane.
Figure 6:
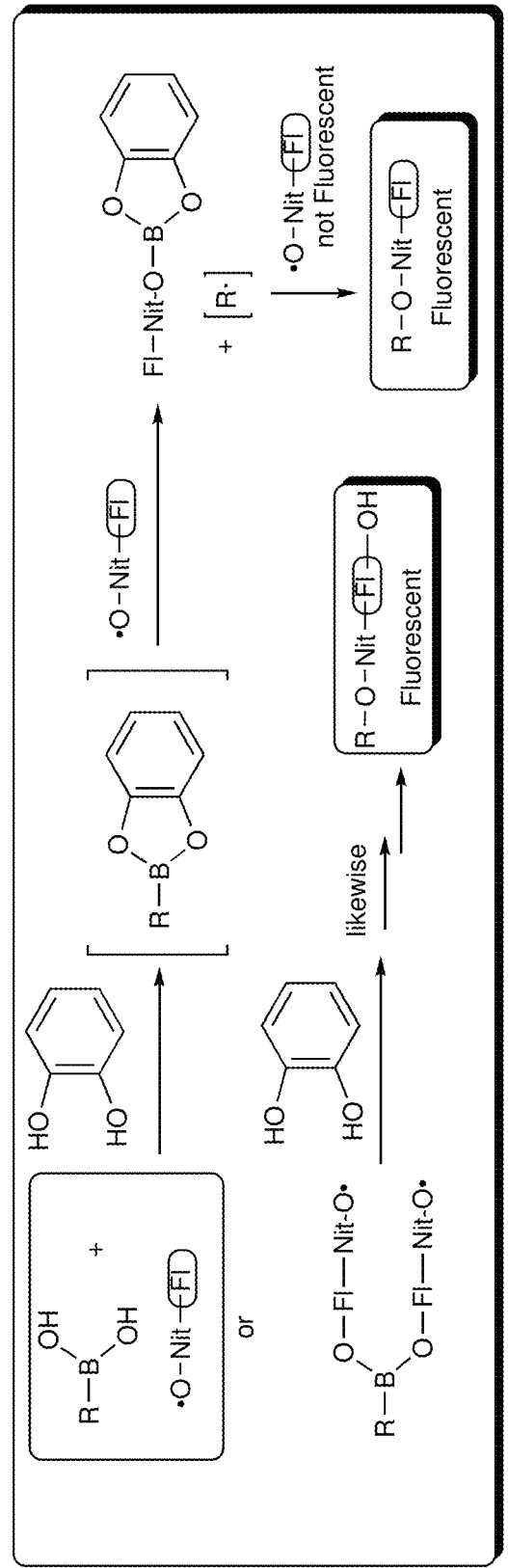
FIG. 6 illustrates an exemplary reaction between a profluorescent nitroxide and a catechol that results in a fluorescent nitroxide-catecholborane.
Figure 8:
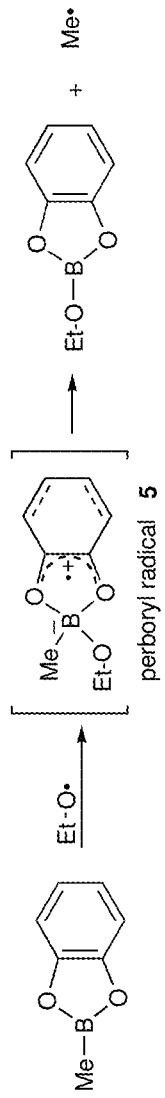
FIG. 8 illustrates that addition of an oxygen radical to an alkylcatecholborane forms a perboryl radical 5, visible by ESR
Figure 9:
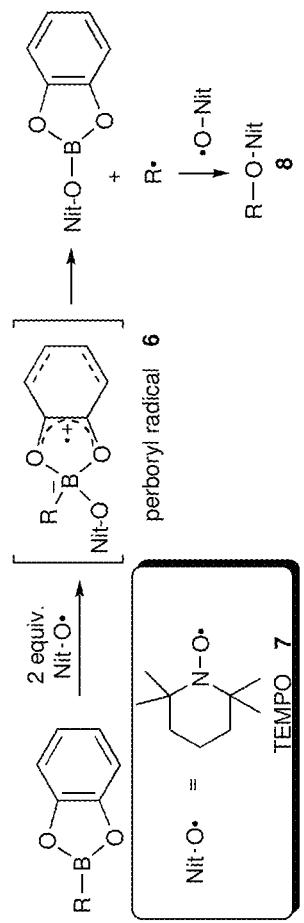
FIG. 9 illustrates that addition of nitroxide to an alkylcatecholborane forms a perboryl radical 6, which fragments to generate an alkyl radical. A second equivalent of nitroxide reacts with the alkyl radical to form alkoxyamine 8.

In order to develop a system to selectively detect catechols in the presence of other alcohols and diols (such as sugars), a reaction that takes place with catechols but not with other alcohols was required. In the field of organic free radical chemistry, alkylcatecholboranes have been used to selectively generate alkyl radicals upon reaction with oxygen radicals. The efficacy of this oxygen radical addition specifically to alkylcatecholboranes is due to de-localization of the unpaired electron of the perboryl species 5 into the aromatic ring (FIG. 8). Direct ESR evidence for this delocalized perboryl radical 5 below 270 K was observed by Roberts (Baban et al., J. Chem. Soc. Perkin Transact. 1986, 2(1): 157-161). A number of very useful synthetic methodologies have been developed from this chemistry. Key to this proposal is the work by Renaud, in which addition of two equivalents of the oxygen radical TEMPO 7, a commercially available persistent nitroxide radical, results in formation of the carbon radical trapping product, alkoxyamine 8 (FIG. 9).

Figure 10:
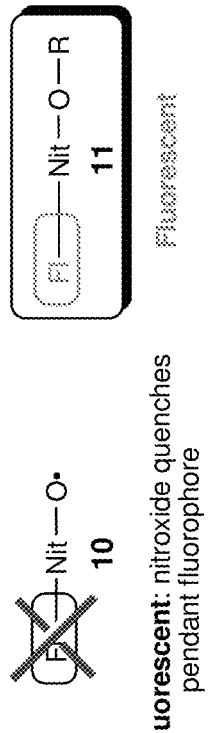
FIG. 10 shows exemplary profluorescent nitroxides: the free nitroxide quenches fluorescence of a closely tethered fluorophore; fluorescence is restored upon reaction to from the alkoxyamine or hydroxylamine.
Figure 11:
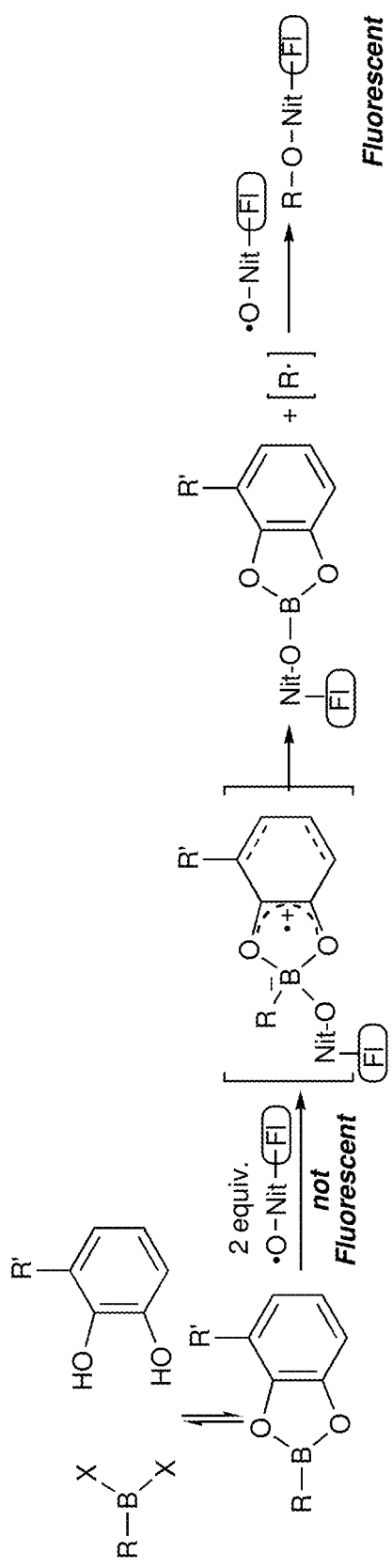
FIG. 11 illustrates a reaction sequence that may detect catechol using profluorescent nitroxide addition to alkylcatecholborane 13.

In order to design a visual indicator of the reaction of nitroxides with alkylcatecholboranes, profluorescent nitroxides are used. Profluorescent nitroxides 10 (sometimes referred to as "pre-fluorescent nitroxides") are nitroxides bearing a short covalent tether to a fluorophore. The free nitroxide quenches the fluorescence. Upon reaction of the nitroxide moiety to form an alkoxyamine 11 or a hydroxylamine (or any other non-nitroxide product), the fluorescence is no longer quenched, restoring fluorescence to the product (FIG. 10). Profluorescent nitroxides have been utilized as sensors of nitric oxide, antioxidants, reactive oxygen species, carbon radicals, cationic metals, viscosity probes, as a chemical logic gate, and in the development of photomagnetic materials. (See Ivan, M. G.; Scaiano, J. C., Photochemistry and Photobiology 2003, 78, (4), 416-419; Hornig, F. S.; Korth, H. G.; Rauen, U.; de Groot, H.; Sustmann, R., Helvetica Chimica Acta 2006, 89, (10), 2281-2296; Lozinsky, E. M.; Martina, L. V.; Shames, A. I.; Uzlaner, N.; Masarwa, A.; Likhtenshtein, G. I.; Meyerstein, D.; Martin, V. V.; Priel, Z., Analytical Biochemistry 2004, 326, (2), 139-145; Meineke, P.; Rauen, U.; de Groot, H.; Korth, H. G.; Sustmann, R., Chemistry—a European Journal 1999, 5, (6), 1738-1747; Meineke, P.; Rauen, U.; de Groot, H.; Korth, H. G.; Sustmann, R., Biological Chemistry 2000, 381, (7), 575-582; Blough, N. V.; Simpson, D. J., Journal of the American Chemical Society 1988, 110, (6), 1915-1917; Lozinsky, E.; Martin, V. V.; Berezina, T. A.; Shames, A. I.; Weis, A. L.; Likhtenshtein, G. I., Journal of Biochemical and Biophysical Methods 1999, 38, (1), 29-42; Tang, Y. L.; He, F.; Yu, M. H.; Wang, S.; Li, Y. L.; Zhu, D. B., Chemistry of Materials 2006, 18, (16), 3605-3610; Hideg, E.; Kalai, T.; Kos, P. B.; Asada, K.; Hideg, K., Photochemistry and Photobiology 2006, 82, (5), 1211-1218; Aspee, A.; Garcia, O.; Maretti, L.; Sastre, R.; Scaiano, J. C., Free radical reactions in poly(methyl methacrylate) films monitored using a prefluorescent quinoline-TEMPO sensor. Macromolecules 2003, 36, (10), 3550-3556; Aspee, A.; Maretti, L.; Scaiano, J. C., Photochemical & Photobiological Sciences 2003, 2, (11), 1125-1129; Ballesteros, O. G.; Maretti, L.; Sastre, R.; Scaiano, J. C., Macromolecules 2001, 34, (18), 6184-6187; Blinco, J. P.; McMurtrie, J. C.; Bottle, S. E., European Journal of Organic Chemistry 2007, 4638-4641; Coenjarts, C.; Garcia, O.; Llauger, L.; Palfreyman, J.; Vinette, A. L.; Scaiano, J. C., Journal of the American Chemical Society 2003, 125, (3), 620-621; Dang, Y. M.; Guo, X. Q., Applied Spectroscopy 2006, 60, (2), 203-207; Fairfull-Smith, K. E.; Blinco, J. P.; Keddie, D. J.; George, G. A.; Bottle, S. E., Macromolecules 2008, 41, 1577-1580; Gerlock, J. L.; Zacmanidis, P. J.; Bauer, D. R.; Simpson, D. J.; Blough, N. V.; Salmeen, I. T., Free Radical Research Communications 1990, 10, (1-2), 119-121; Johnson, C. G.; Caron, S.; Blough, N. V., Analytical Chemistry 1996, 68, (5), 867-872; Maurel, V.; Laferriere, M.; Billone, P.; Godin, R.; Scaiano, J. C., Journal of Physical Chemistry B 2006, 110, (33), 16353-16358; Micallef, A. S.; Blinco, J. P.; George, G. A.; Reid, D. A.; Rizzardo, E.; Thang, S. H.; Bottle, S. E., Polymer Degradation and Stability 2005, 89, (3), 427-435; Nagy, V. Y.; Bystryak, I. M.; Kotelnikov, A. I.; Likhtenshtein, G. I.; Petrukhin, O. M.; Zolotov, Y. A.; Volodarskii, L. B., Analyst 1990, 115, (6), 839-841; Arye, P. P.-B.; Strashnikova, N.; Likhtenshtein, G. I., Journal of Biochemical and Biophysical Methods 2002, 51, (1), 1-15; and Wang, H. M.; Zhang, D. Q.; Guo, X. F.; Zhu, L. Y.; Shuai, Z. G.; Zhu, D. B., Chemical Communications 2004, (6), 670-671.)

The use of a profluorescent nitroxide with an alkylboronic acid derivative 12 is envisioned to react with catechols (such as, but not limited to, for example, urushiol) to form alkylboronate 13: nitroxide addition, radical 14 generation, and nitroxide trapping will generate the fluorescent signal of alkoxyamine 15. Other alkylboronic acid derivatives will be apparent to those of skill in the art.

Catechols are a group of compounds well-known to those of skill in the art having diverse biological activities, whilst at the same time being structurally conservative. The invention contemplates that the compositions and methods disclosed herein may be used to detect, inactivate, or bind to any biologically-active catechol composition. In particular the invention contemplates a catechol selected from the group consisting of urushiol, catechin, epicatechin, gallocatechin, epigallocatechin, epigallocatechin-3-gallate, and catecholamines epinephrine, norepinephrine, dopamine, and dihydroxyphenylalanine (DOPA). One of skill in the art would consider that the structures of catechols are sufficiently similar that they are a well-known chemical class of compounds.

Profluorescent nitroxide is sometimes referred to as a prefluorescent nitroxide. In the presence of a catechol such as urushiol and an B-alkylboronic acid derivative, a B-alkyl catecholborinate is formed. Addition of the nitroxide to the catecholborane results in expulsion of an alkyl radical, which is trapped by a second nitroxide, forming two fluorescent species: an alkoxyamine with a fluorescent tag, and fluorescently tagged nitroxide-catecholborane complex. In addition, the nitroxide-catecholborane may degrade to hydroxylamine that is also a fluorescent compound. Use of a hand-held fluorescent lamp shows fluorescence when a catechol such as urushiol is present. This can be used as a method to detect the presence of urushiol. As a treatment, binding of the urushiol into a catecholborane complex will prevent transfer through the skin, preventing oxidation of the catechol and elicitation of an immune response, thus preventing contact dermatitis. For detecting aqueous soluble catechols such as dopamine, epinephrine, and norepinephrine, a water-soluble alkyl group is preferred on the initial boron compound rather than a hydrophobic alkyl group.

Examples of profluorescent nitroxides may be found in the following non-exhaustive list of publications: Blough, 1988, JACS, 110: 1915; Bottle, 2005, Polym. Degrad. & Stability, 89: 427-435; Sciano, 2001, Macromol. 34: 6184; Ibid., 2003, JACS, 125: 620; Ibid., 2003, Photochem. Photobiol. 78: 416; Turro, 2001, Macromol., 34: 8187; Koth, 2000, Biological Chem., 381(7): 575-582; Ibid., 1999, Chem. Eur. J. 5(6): 1738-1747; Ibid., 1997, Ang. IEE, 36: 1501-1503; Ibid., 2006, Helv. Chim Acta, 89: 2281-2296; Hideg 2006, Photochem. Photobiol. 82: 1211; Want, 2006, Chem. Mater., 18: 3605; and Dang and Guo, 2006, Appl. Spectrosc. 60: 203-207, In the present invention, a non-limited list of quantum dot nanoparticles includes cadmium sulfide (CdS), cadmium selenide (CdSe), zinc sulfide (ZnS), zinc oxide (ZnO), lead sulfide (PbS), zinc selenide (ZnSe), GaAS, and InP. (Lakowicz et al. Analytical Biochemistry, 2000, 280: 128-136). Alternative suitable donor fluorophores will be apparent to those of ordinary skill without undue experimentation. For example, nitroxides tethered to such a quantum dot will quench any fluorescence; when the nitroxides react with a catechol boronate complex, the quenching effect is removed and fluorescence can occur under appropriate conditions.

Use of the Compositions for Detection of Urushiol

A composition prepared according to the present invention may be formulated as an aerosol spray, a topical cream, ointment, medicament, or a solution.

An aerosol containing approximately 0.005% to about 5.0% (w/w) each of the boron composition and nitroxide according to the present invention is prepared by dissolving the compositions in absolute alcohol. The resulting solution is then diluted in an organic solvent or purified water, depending upon the hydrophobicity of the compound. Routine experimentation by those having skill in the art can be used to determine an effective amount for detecting a catechol in a sample.

There are several biologically very important catechols: the catecholamines (including epinephrine, norepinephrine, and dopamine), in addition to epicatechin (common in tea). All of these are water-soluble. Because boron species undergo dynamic exchange of alcohol ligands via their anionic "-ate" species in water, it is likely that this methodology may be extrapolated to detect catechols in an aqueous environment. The key reaction sequence of nitroxide reacting with alkylcatecholborane is well established in non-polar organic solvents. Extension to aqueous conditions would provide a very powerful detection method for catecholamines: success would depend on the lifetimes of the tricoordinate borane species compared to the predominate tetracoordinate boronate species. Water-soluble nitroxides and fluorophores are widely known; nitroxides have been used extensively as an EPR probe in biology. The detection of biologically important catecholamines (including epinephrine, norepinephrine, and dopamine) in aqueous environments could lead to powerful new methods in biomedicine.

Contact dermatitis from exposure of skin to urushiol causes agony and suffering for tens of millions of Americans each year, making this an important human health issue in North America. Urushiol can be effectively removed from skin, clothes and equipment, but only if it is known where this invisible contamination is located. The invention comprises a fluorescence detection method: a spray containing a profluorescent nitroxide and an alkylboronate derivative in an organic solvent will react selectively with urushiol to form a fluorescent N-alkoxyamine. An inexpensive UV light can then be used to pinpoint the presence of urushiol, to prevent or mitigate exposure to skin. Preliminary results with catechol confirm that the key reaction works as expected, and that a highly fluorescent signal is generated. Optimization of the profluorescent nitroxide (both the fluorophore and nitroxide structures), solvent and fine-tuning of the alkyl group on the boronic acid are undertaken. The invention provides a clear benefit to society, including private outdoors enthusiasts, forestry workers, emergency rescue personnel, military personnel, and others who come in contact with poison oak, poison ivy, or sumac.

The invention also may be used to deactivate a chatechol, such as urushiol, using the methods disclosed herein. In certain case the product, such as B-alkyl catecholboronate or alkycatecholborane, may be chemically unstable and the composition may hydrolyse to the products, chatechol and the alkylboronate derivative, for example. It is contemplated that such hydrolysis may be impeded or decelerated in the presence of environmental modulators, such as a hydrophobic composition, a hydrophilic composition, a buffer composition, or the like. Such environmental modulators can be sugars, carbohydrates, proteins, peptides, glycopeptides, glycolipids, and glycophospholipids; organic compositions, such as organic acids, organic salts, organic bases, or the like, lipids, phospholipids, or fatty acids; chemical stabilizers, or the like, or any combination thereof. Such compositions may be used to formulate a topical medicament or topical composition that is used to reduce or eliminate the effects of poison oak oil-induced contact dermatitis.

In addition, the formulation or aerosol can comprise a solvent, the solvent comprising a polar organic solvent, a non-polar organic solvent, an aqueous solvent, or a non-aqueous solvent.

The invention will be more readily understood by reference to the following examples, which are included merely for purposes of illustration of certain aspects and embodiments of the present invention and not as limitations.

EXAMPLES

Example I

Preparation and Testing of Fluororescent Compounds

Figure 12:
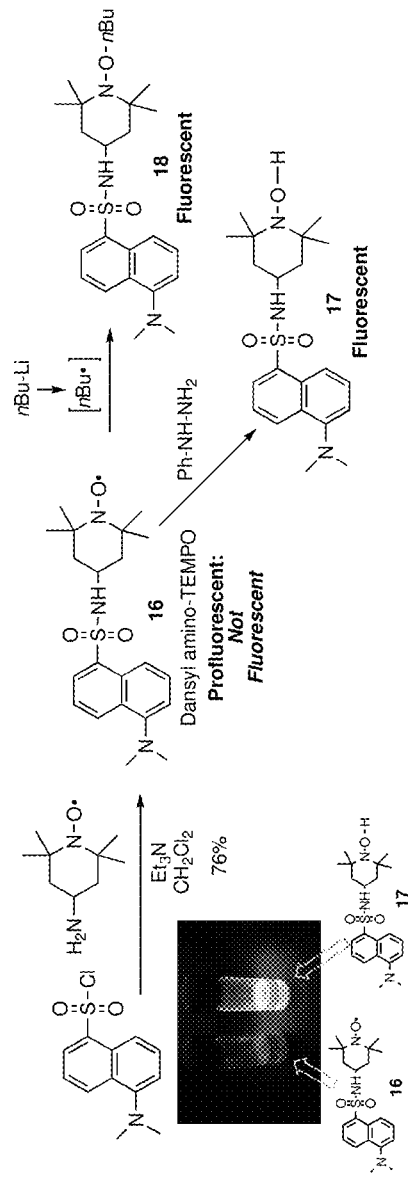
FIG. 12 illustrates use of profluorescent Dansyl amino-TEMPO: preparation, reduction, and formation of radical trapping product 17.

We have prepared the known profluorescent nitroxide Dansyl amino-TEMPO 16. As reported, the free nitroxide quenches fluorescence; the insert of FIG. 12 shows the reaction of the nitroxide to form either the hydroxylamine 17 (vial shown) or the n-butylalkoxyamine 18 (not shown) restores the fluorescence to the naked eye upon irradiation with a long wave-length UV lamp at 366 nm (A hand-held UV lamp typically used for viewing thin layer chromatography plates was utilized in these photographs).

Figure 13:
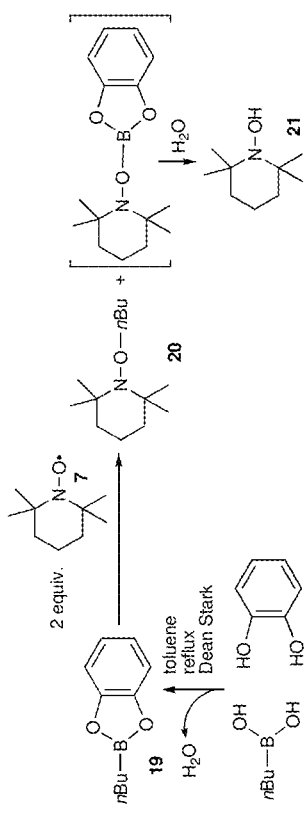
FIG. 13 shows an exemplary reaction of a model alkyl-catecholborane 19 with two equivalents of nitroxide: both alkoxyamine 20 and hydroxylamine 21 were isolated from the reaction mixture.

As an initial model, B-n-butylcatecholborane 19 was preformed using Dean Stark conditions, and then allowed to react with two equivalents of TEMPO 7 (FIG. 13). The expected N-n-butyloxyamine 20 was formed as a mixture with the hydroxylamine 21, confirming the chemistry developed by Renaud. Hydroxylamine 21 is presumably formed by hydrolysis of the nitroxide boronic ester complex.

Figure 14:
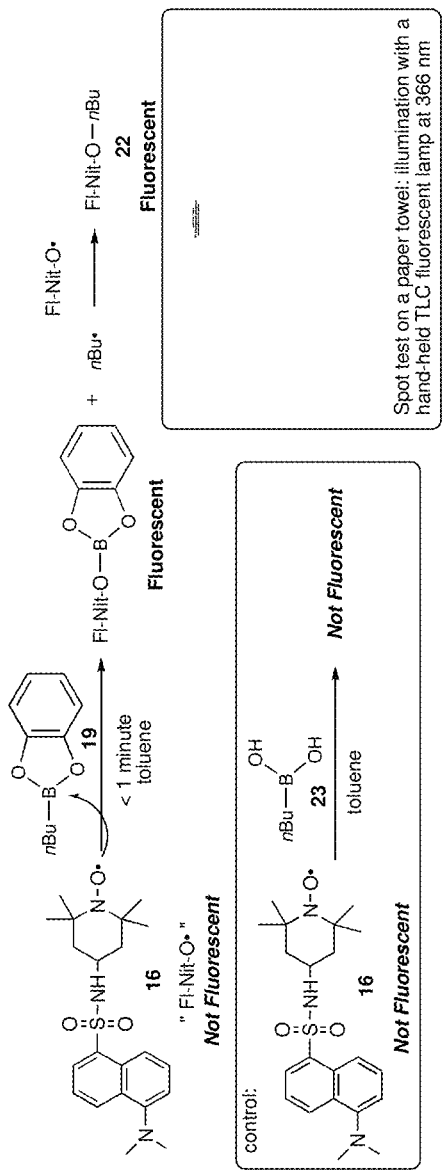
FIG. 14 illustrates reaction of profluorescent Dansyl amino-TEMPO 16 with n-butylcatecholborane 19 in toluene to give fluorescent n-butylalkoxyamine 22 (A): paper towel spot test shows fluorescence of alkoxyamine 22 (B).

This reaction was repeated with the profluorescent Dansyl amino-TEMPO 16 (FIG. 14A). The reaction mixture was strongly fluorescent in which a drop of solution was put on a paper towel; illumination with a thin layer chromatography (TLC) long-wavelength lamp clearly showed a strong fluorescent signal for the alkoxyamine 28 (see FIG. 14B). Similar drops of solution containing the profluorescent nitroxide 16 and a control mixture of the profluorescent nitroxide mixed with n-butylboronic acid gave no detectible signal. Isolation and characterization of the fluorescent n-butylalkoxyamine 22 confirmed that the reaction had occurred as predicted.

Example II

Fluorescence Detection of Catechol

In order to form alkylcatecholborane 13 from free catechol under ambient conditions, we initially believed it would be necessary to convert the hydroxyl groups on an alkylboronic acid to better leaving groups. However, early work by Brown indicated that alkylboronic acids react reversibly with catechol in organic, nonpolar solvents to form the desired catecholboranes. It was determined that the reaction sequence shown in FIG. 15A worked: alkylcatecholborane 19 formed from free catechol and an alkylboroinic acid in situ, and reacted with profluorescent nitroxide 16 in one pot to form 22 with a strongly fluorescent signal (FIG. 15B). This was an unexpectedly superior result.

Figure 26:
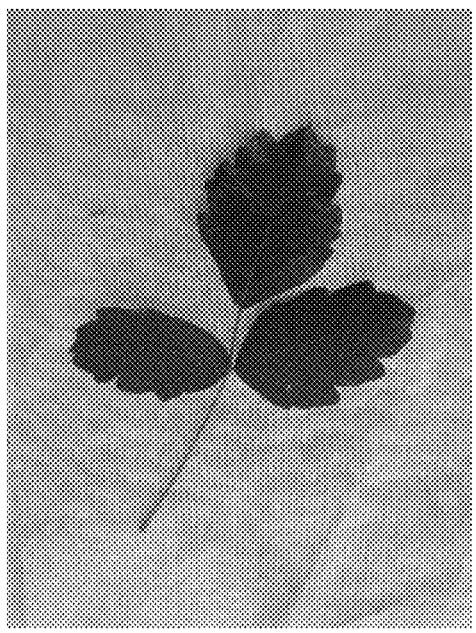
FIG. 26 illustrates detection of urushiol on leaves of poison oak. A: Fresh Poison Oak triad of leaves; B: Print of the same leaves on a paper towel after treatment with Fl-NitO., nBuB(OH)$_2$ and catalytic $PbO_2$ in acetone.
Figure 26:
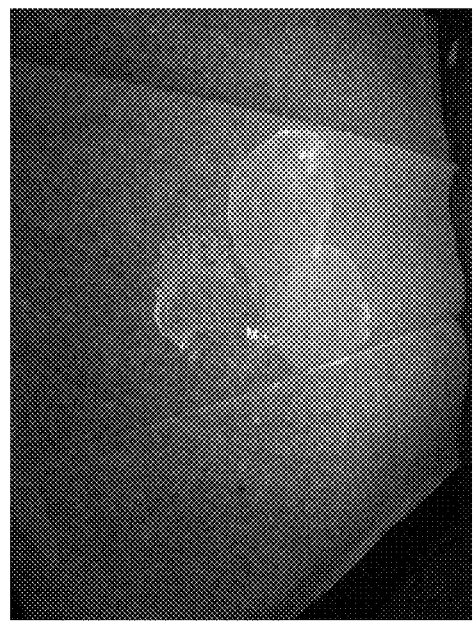

FIG. 26 shows a successful field test of this detection system. The composition was applied onto the surface of poison oak leaves. A paper towel was applied to the surface of the leaves and the paper towel was illuminated using a UV-lamp. As shown in FIG. 26, the fluorescence was clearly visible to the naked eye.

It has also been observed that the reaction works well in a variety of polar and nonpolar solvents.

Example III

Synthesis and Development of the Components of the Fluorescence-Generation Method: Optimize the Structure of the Nitroxide, Fluorophore, Tether and Alkylboronic Acid The chemical design of the profluorescent nitroxide is explored, entailing the choice of the optimum nitroxide, fluorescent tag, and tether to prepare a robust, soluble and effective component for this detection system. As fluorescence is a very sensitive method of detection, only very small amounts need react to give a signal visible to the naked eye using an inexpensive hand-held fluorescent lamp. The six-membered ring TEMPO is by far the most common nitroxide scaffold, however there are a number of other common stable nitroxide classes. Considerations in optimization of the nitroxide structure include ease and cost of synthesis, versatility in designing and optimizing the tether between the fluorophore and the nitroxide, stability and solubility. Common stable nitroxide classes include TEMPO (tetramethylpiperidinyl-1-oxyl), proxyl (pyrrolidine analogues), nitronyl, imino and doxyl nitroxides (FIG. 16). The inventor and the inventor's research laboratory has been engaged in the synthesis and applications of nitroxides for over a decade, thus has extensive experience in the synthesis of new nitroxides. In addition, a large number of commercially nitroxides are available from Toronto Research Chemicals, Inc. (North York, Canada).

Recent work by Lozinsky et al. (2004) indicates that profluorescent nitronyl nitroxides quench fluorescence by a different mechanism involving nonbonding electrons of nitrogen and oxygen rather than to the unpaired electron. Thus the fluorescence does not increase upon reduction to the hydroxylamine (and also presumably from the formation of alkoxyamines), making them unsuitable for this study. Given the simple synthetic access (FIG. 17) to proxyl nitroxides following the large body of work pioneered by Hideg, Keana, and many others, proxyl nitroxides 42 are particularly attractive.

Figure 18:
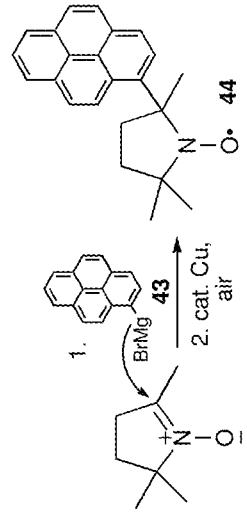
FIG. 18 shows the synthesis of the pyrene proxyl profluorescent nitroxide 44.

The fluorophore can be easily introduced late in the synthetic sequence, encouraging synthetic diversity without having to start the sequence from the beginning. For an example, a Grignard reagent 43 prepared from 1-bromopyrene gives the proxyl nitroxide 44 with a very short tether between the fluorophore and the nitroxide (FIG. 18).

Example IV

Use of Fluorescence Detection

Figure 19:
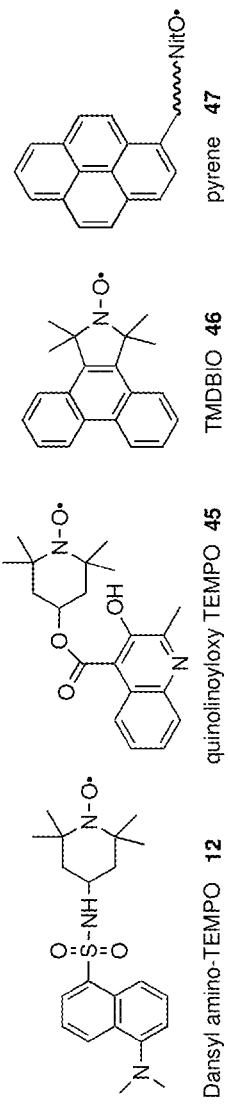
FIG. 19 illustrates a few representative known profluorescent nitroxides.

With regard to the choice of fluorophore, preliminary data and results focused on Dansyl amino-TEMPO 12, a well-developed profluorescent nitroxide. One advantage of this compound is that sulfonamides are resistant to hydrolysis, thus minimizing the possibility of hydrolysis to give a free fluorophore and thus a false positive signal. Scaiano (Aliaga et al., Organic Lett., 2003, 5(22): 4145-4148) has developed 4-(3-hydroxy-2-methyl-4-quinolinoyloxy)-TEMPO 45, which shows significantly enhanced fluorescence upon reaction of the nitroxide compared to Dansyl amino-TEMPO 12 (but contains a more easily hydrolyzed ester linkage) (FIG. 19). Bottle (Micallef et al., Polymer Degrad. Stabil., 2005, 89(3): 427-435) has developed the profluorescent nitroxide TMDBIO 46, containing a phenanthrene fluorophore covalently fused into the structure of the nitroxide, making hydrolysis an impossibility. Other fluorophores such as pyrene 47 and coumarins have been utilized, and many more are possible. The use of fluorophores observable in the visible range is also explored. The intensity, wavelength dependence, cost, stability and ease of synthesis will all be taken into consideration in selecting the best fluorophore.

Efficient quenching requires a short tether between the fluorophore and the nitroxide moiety; rotational freedom and flexibility also influence the quenching efficiency. Thus the 5-membered ring nitroxides may provide an advantage in holding the fluorophore in a closer geometry to the nitroxide as compared to the 6-membered ring framework of TEMPO.

Example V

Quenching of Fluorophore

Figure 20:
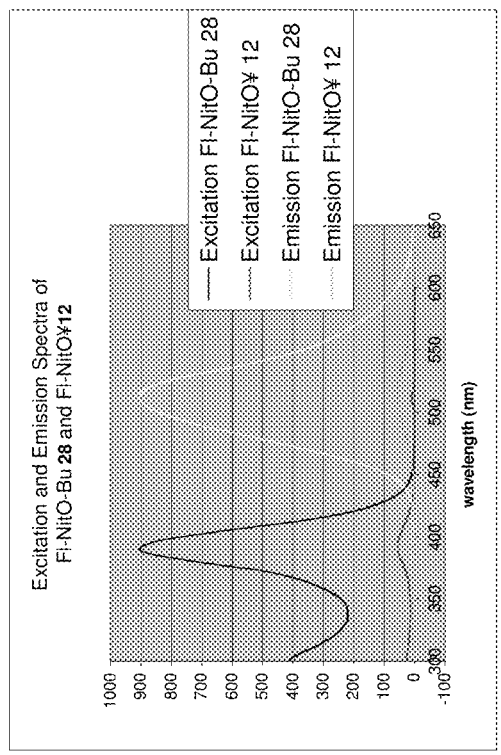
FIG. 20 illustrates the excitation and emission spectra of profluorescent nitroxide 12 and fluorescent N-alkoxyamine 28 in DMSO.

Dansyl amino TEMPO 12 does show a small amount of residual fluorescence, as shown in FIG. 20. Other profluorescent nitroxides may be even more effective at quenching the fluorescence in the free nitroxide state. The wavelength of excitation and emission can be tuned by selection of the fluorophore.

Example VI

Effect of Charge Upon Fluororescence Detection

Figure 21:
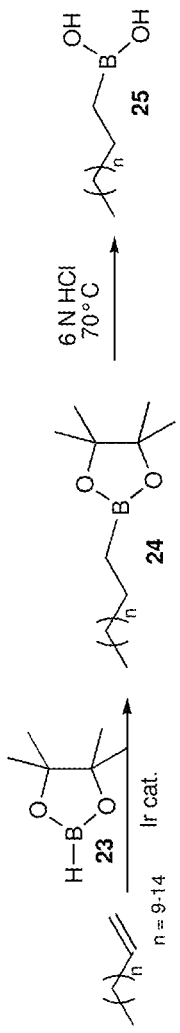
FIG. 21 shows a hydroboration route to prepare n-alkylboronic acids 25

Since urushiol is very hydrophobic, apolar organic solvents are investigated for the key reaction sequence, including toluene, hexanes, acetone, ethers, etc. The linear hydrophobic "tail" is optimized for both reactivity with catechol and solubility to match that of the hydrophobic urushiol. B-alkylpinacolboranes 24 are conveniently prepared by iridium-catalyzed hydroboration[78] of the corresponding terminal alkenes using commercially available pinacolborane 23 (FIG. 21). Hydrolysis provides easy access to alkylboronic acids with a variety of chain lengths. Commercially available $C_{12}$-$C_{17}$ linear terminal olefins are available, with the $C_{14}$ and $C_{16}$ being particularly inexpensive. Upon testing with actual urushiol, there may be an advantage to having an odd or even number of carbons in the sidechain, or the exact carbon count may prove to be inconsequential. The stability of the boronic acid is also a consideration. Tertiary alkyl boronic acids are prone to decomposition upon exposure with air. In our preliminary studies, we have used primary n-butyl boronic acid. The sample has remained stable for over a year without taking any precautions to avoid exposure to air. We have determined that aryl boronic acids (very stable, and commercially available) do not take part in the radical reaction sequence, presumably due to failure of the fragmentation step due to the instability of aryl radicals. Thus primary alkyl boronic acids seem to be ideal: they react in the desired radical reaction sequence, but are stable to storage.

Example VII

Optimizing the Detection System with Regard to Stoichiometry, Solvent, Concentration, Reaction Time, and Avoidance of False Positives Calibration of the fluorescence signal as a function of the concentration of the catechol, boron reagent and nitroxide is carried out. As exposure to 0.001 mg of urushiol can elicit allergic contact dermatitis, very small amounts of urushiol should to be detectable to make this method effective. The optimal stoichiometry to obtain a short reaction time is studied. It is expected that two nitroxides are needed for every boron complex, although one equivalent may be sufficient if the nitroxide catecholboronate complex is hydrolytically unstable. If the fluorescent signal is extremely strong, it may be possible to economize by using a mixture of regular nitroxide mixed with some small percentage of profluorescent nitroxide.

Figure 22:
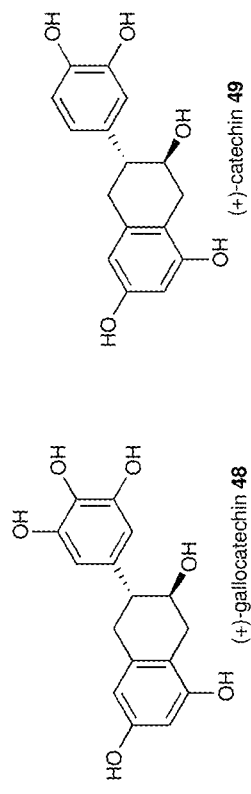
FIG. 22 illustrates representative pyrogallols and catechols commonly found in foods such as red wine, tea, and chocolate: note that compounds 48 and 49 are polyols, and are thus aqueous rather than organic soluble.

The specificity of this system for catechols is explored. As controls, phenols, resorcinols (1,3-benenediols), alcohols and diols (for example, sugars) are not expected to participate in the key reaction sequence, as no delocalized perboryl radical intermediate similar to 6 will be formed. Reaction with these various alcohols are tested to ensure that this method is indeed selective for catechols. Pyrogallols (1,2,3-benenetriols, for example gallocatechins (ex. 48) and epigallocatechins (FIG. 22) found in red wine, tea and chocolate) are expected to participate in the reaction, depending upon their solubility in the solvents. Likewise, the closely related catechins (ex. 49) and epicatechins (found in foods along with gallocatechins) are true catechols: reactions are again be limited by solubility.

Figure 23:
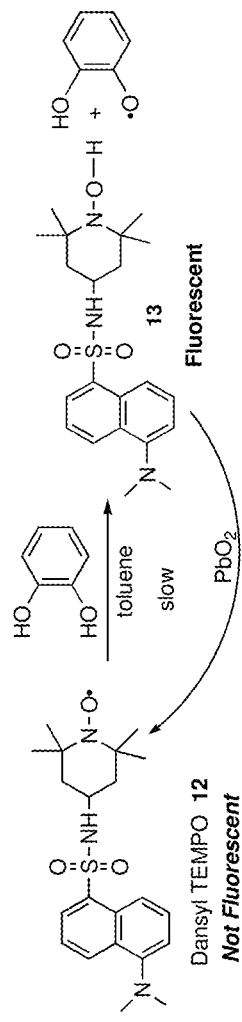
FIG. 23 illustrates a slow reduction of nitroxide by catechol; rapid reoxidation of the hydroxylamine to the nitroxide with $PbO_2$.

Possible sources of false positives are examined. It is well known that nitroxides react rapidly with ascorbic acid to form hydroxylamines. Our research group has used ascorbate reduction of nitroxide to aid in chromatographic separation of alkoxyamine from unreacted nitroxide. Blough was the first to show profluorescent nitroxides react with ascorbic acid to generate a fluorescent signal. Lozinsky has utilized profluorescent nitroxides to assay the amount of vitamin C in fruit juices, and Wang has used a fluorescent conductive charged polymer nitroxide salt as a sensor for ascorbate and for trolox (a vitamin E mimic) Another side reaction that may interfere with the selective detection of urushiol by this boron catechol sequence is the simple reduction of nitroxides by phenols. Scaiano has studied the kinetics of hydrogen transfer from phenol to nitroxide using a profluorescent nitroxide. The rate constants are very slow: k=0.003 $M^{-1}s^{-1}$ in protic solvent for gallic acid and BHT, and k=0.2 $M^{-1}s^{-1}$ for TROLOX. Scaiano did not investigate reduction by catechol. In preliminary experiments (FIG. 23), we have shown that addition of catechol to Dansyl amino-TEMPO 12 in toluene does produce a weak fluorescent signal, however this is suppressed by addition of a mild oxidant ($PbO_2$) to convert the tiny amount of hydroxylamine to nitroxide. This removes the false positive from phenol (FIG. 24).

Figures 24, 25:
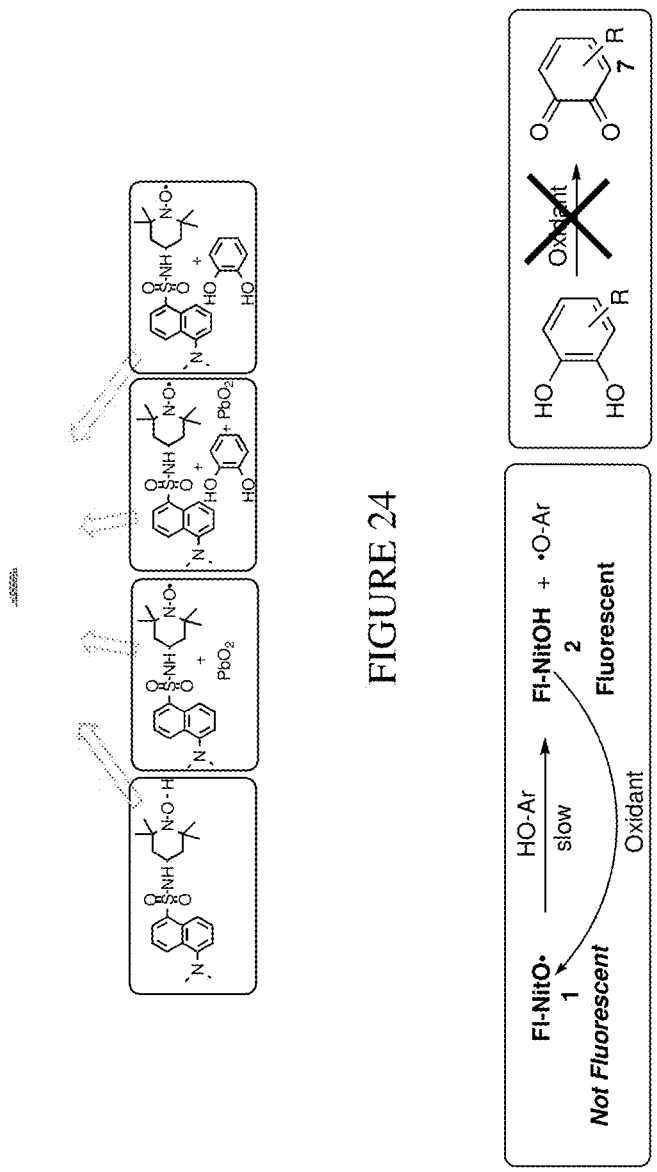
FIG. 24 illustrates fluorescence quenching and recovery upon addition of catechol to profluorescent nitroxide 12, with and without addition of $PbO_2$ as a reoxidant.
FIG. 25 illustrates how exemplary mild oxidants can rapidly oxidize hydroxylamine to nitroxide but that do not oxidize catechol to quinone.

The use of other mild oxidants that will rapidly oxidize hydroxylamine to nitroxide in organic solvents, but not oxidize catechol to quinone, are investigated (See FIG. 25). Particularly attractive are $Fe^{(III)}$ salts as less toxic alternatives to lead. We have determined that OXONE is too strong of an oxidizing agent: the nitroxide is oxidized to the oxammonium salt. Interestingly, Bottle has shown that pyrrolidine nitroxides (cyclic 5-membered rings) have higher reduction potentials than piperidine (6-membered ring) nitroxides. Thus use of a pyrrolidine profluorescent nitroxide may inhibit the false positive signal arising from reduction by phenols.

REFERENCES

Addition of Nitroxides to Catecholboranes:
Schaffner and Renaud (2004) Eur. J. Org. Chem. 2291-2298.
Darmency and Renaud, (2006) Top. Curr. Chem. 263: 71-106.
Cadot et al., (2002) J. Org. Chem., 67; 7193-7202.
Ollivert et al. (1999) Synlett. 6: 807-809.
Attempted Addition of Nitroxides to Trialkylboranes:
Braslau and Anderson, in *Radicals in Organic Synthesis*, vol. 2 (Eds. P. Renaud, M. P. Sibi), Wiley-VCH, Weinheim, 2001, p. 129.
Addition of Oxygen Radicals to Catecholboranes:
Baban et al. (1986) J. Chem. Soc., Perkin Trans 2: 157.
Suzuki et al. (1969) J. Chem. Soc., Chem. Commun 1009.
Brown and Negishi (1971) J. Am. Chem. Soc. 93: 3777.
Forster (1999) PhD Thesis, Université de Fribourg, Switzerland, Diss. Nr. 1242.
Ollivier and Renaud (1999) Chem. Eur. J. 5: 1468.
Kumli et al. (2006) Organic Lett. 8(25): 5861-5864.
Ollivier and Renaud (2000) Angew. Chem. Int. Ed. Eng. 39: 925.
Profluorescent Nitroxides:
Blough (1988) J. Am. Chem. Soc. 110: 1915.
Blough (1990) Free Rad. Res. Comm 10: 119-121.
Blough (1996) Anal. Chem. 68: 867-872.
Micallef A S et al. (2005) Polym Degrad. & Stability 89: 427-435.
Foitzik et al. (2008) Macromolecules 41: 1577-1580.
Blinco et al. E. J. Org. Chem. 28: 4638-4641.
Sciano (2001) Macromol. 34: 6184.
Coenjarts et al. (2003) J. Am. Chem. Soc 125: 620-621.
Ivan et al. (2003) Photochem. Photobiol. 78: 416.
Aspee et al. (2007) Photochem. Photobiol. 83(3): 481-485.
Maurel et al. (2006) J. Phys. Chem. B, 110(33): 16353-16358.
Laferriere et al. (2006) Chem. Comm (3): 257-259.
Aspee et al. (2003) Photochem. Photobiol. Sci. 2(11): 1125-1129.
Aspee et al. (2003) Macromolecules, 36(10): 3550-3556.
Korth (2000) Biol. Chem. 381(7): 575-582; ibid (1999) Chem. Eur. J. 5(6): 1738-1747;
ibid (1997) Angew. Chem. Int. Ed. Eng. 36: 1501-1503; ibid (2006) Helv. Chim Acta 89: 2281-2296.
Zhang and Zhu (2004) Chem. Commun 670.
Hideg (2006) Photochem. Photobiol. 82: 1211.
Wang (2006) Chem. Mater. 18: 3605-3610.
Dang and Guo (2006) Appl. Spectrosc. 60: 203-207.
Likhtenstein et al. (2007) Photochem. Photobiol. 83: 871-881.
Lozinsky, et al. (2004) Anal. Biochem. 326: 139-145.
Likhtenstein (2002) Biochem. Biophys. Meth. 51: 1-15.
Likhtenstein (1990) Analyst 115: 839.
Likhtenstein (1999) Biochem. Biophys. Meth. 38: 29-42.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

I claim:

1. A catechol detecting kit, the catechol detecting kit comprising a compound, a suitable excipient, carrier, or combination thereof, an applicator, a vessel, the vessel shaped and adapted for confining the compound, the compound comprising a nitroxide and an effective amount of a boron compound, the boron compound comprising an alkylboronic acid having the general formula R—$B(OH)_2$, and wherein the boron compound is in an effective amount for detecting a catechol.

2. The catechol detecting kit of claim 1, wherein the boron compound comprises a hydrophobic alkyl group.

3. The catechol detecting kit of claim 1, wherein the boron compound comprises a hydrophilic alkyl group.

4. The catechol detecting kit of claim 1, wherein the nitroxide is a profluorescent nitroxide.

5. The catechol detecting kit of claim 1, wherein the applicator is a spray applicator.

6. The catechol detecting kit of claim 1, wherein the catechol is urushiol.

7. The catechol detecting kit of claim 1 further comprising an aerosol propellant.

8. The catechol detecting kit of claim 1 further comprising a lamp.

9. The catechol detecting kit of claim 1, wherein the boron compound optionally comprises at least one B-alkyl boronic acid derivative.

10. The catechol detecting kit of claim 1 wherein the boron compound is present in an amount selected from the group consisting of from about 99.5% to about 0.001%, from about 95% to about 0.1%, and from about 90% to about 0.5%, by weight, based on the total combined weight of the boron composition thereof.

11. The catechol detecting kit of claim 1, wherein the catechol is a catechol in poison oak oil.

12. A catechol detecting kit, the catechol detecting kit comprising a compound, a suitable excipient, carrier, or combination thereof, an applicator, a vessel, the vessel shaped and adapted for confining the compound, the compound comprising a nitroxide and a boron compound, the boron compound comprising an alkylboronic acid having the general formula R—B(OH)$_2$, where R is selected from the group consisting of a hydrophobic alkyl group and a hydrophilic alkyl group, and wherein the boron compound is in an effective amount for detecting a catechol.

13. The catechol detecting kit of claim 12, wherein the nitroxide is a profluorescent nitroxide.

14. The catechol detecting kit of claim 12, wherein the applicator is a spray applicator.

15. The catechol detecting kit of claim 12, wherein the catechol is urushiol.

16. The catechol detecting kit of claim 12 further comprising an aerosol propellant.

17. The catechol detecting kit of claim 12 further comprising a lamp.

18. The catechol detecting kit of claim 12, wherein the boron compound optionally comprises at least one B-alkyl boronic acid derivative.

19. The catechol detecting kit of claim 12 wherein the boron compound is present in an amount selected from the group consisting of from about 99.5% to about 0.001%, from about 95% to about 0.1%, and from about 90% to about 0.5%, by weight, based on the total combined weight of the boron composition thereof.

20. The catechol detecting kit of claim 12, wherein the catechol is a catechol in poison oak oil.

21. The catechol detecting kit of claim 1, where R is selected from the group consisting of a hydrophobic alkyl group and a hydrophilic alkyl group.

22. The catechol detecting kit of claim 1, further comprising a set of instructions for how to use the catechol detecting kit.

23. The catechol detecting kit of claim 12, further comprising a set of instructions for how to use the catechol detecting kit.

* * * * *